United States Patent [19]

Seith et al.

[11] Patent Number: 4,599,996
[45] Date of Patent: Jul. 15, 1986

[54] LEG MANIPULATING DEVICE

[76] Inventors: Nancy Seith, 8800 Carmichael Dr., Chesterland, Ohio 44026; Robert C. Johnson, 151 Carriage Dr., Apt. 101, Chagrin Falls, Ohio 44022

[21] Appl. No.: 671,480

[22] Filed: Nov. 14, 1984

[51] Int. Cl.$^4$ .............................................. A61H 1/02
[52] U.S. Cl. .................................. 128/25 R; 128/25 B; 272/70
[58] Field of Search ....................... 128/25 R, 25 B, 68, 128/80 R, 80 F, 80 G, 83.5; 135/65–68, 71–76; 272/70, 70.3; 273/80 D

[56] References Cited

U.S. PATENT DOCUMENTS

| 1,253,700 | 1/1918 | McLaughlin | 273/80 D |
| 1,608,032 | 11/1926 | McNabb | 128/80 G |
| 1,663,921 | 3/1928 | Pierce | 128/84 R |
| 2,966,905 | 1/1961 | Kamenshine | 128/25 R |
| 3,502,071 | 3/1970 | Holly | 128/25 R |
| 3,923,045 | 12/1975 | Talati et al. | 128/25 R |

Primary Examiner—Vincent Millin
Assistant Examiner—J. Welsh
Attorney, Agent, or Firm—Baldwin, Egan & Fetzer

[57] ABSTRACT

A device for facilitating the movement by a patient of an incapacitated limb comprising, a base adapted to be supported on the thigh of the patient's limb, a lever pivoted to the base, a lifter member attached to the lever and adapted for coupling to the patient's limb generally adjacent the distal end thereof, for connecting the limb to the lever, thereby enabling the patient to shift the incapacitated limb by acutuation of the lever, and wherein the lever and the lifter member include manually actuatable mechanism for selectively adjusting the lengths thereof, for accommodating the device to different sizes of patients. The lever also includes an adjustable projecting handle portion.

17 Claims, 18 Drawing Figures

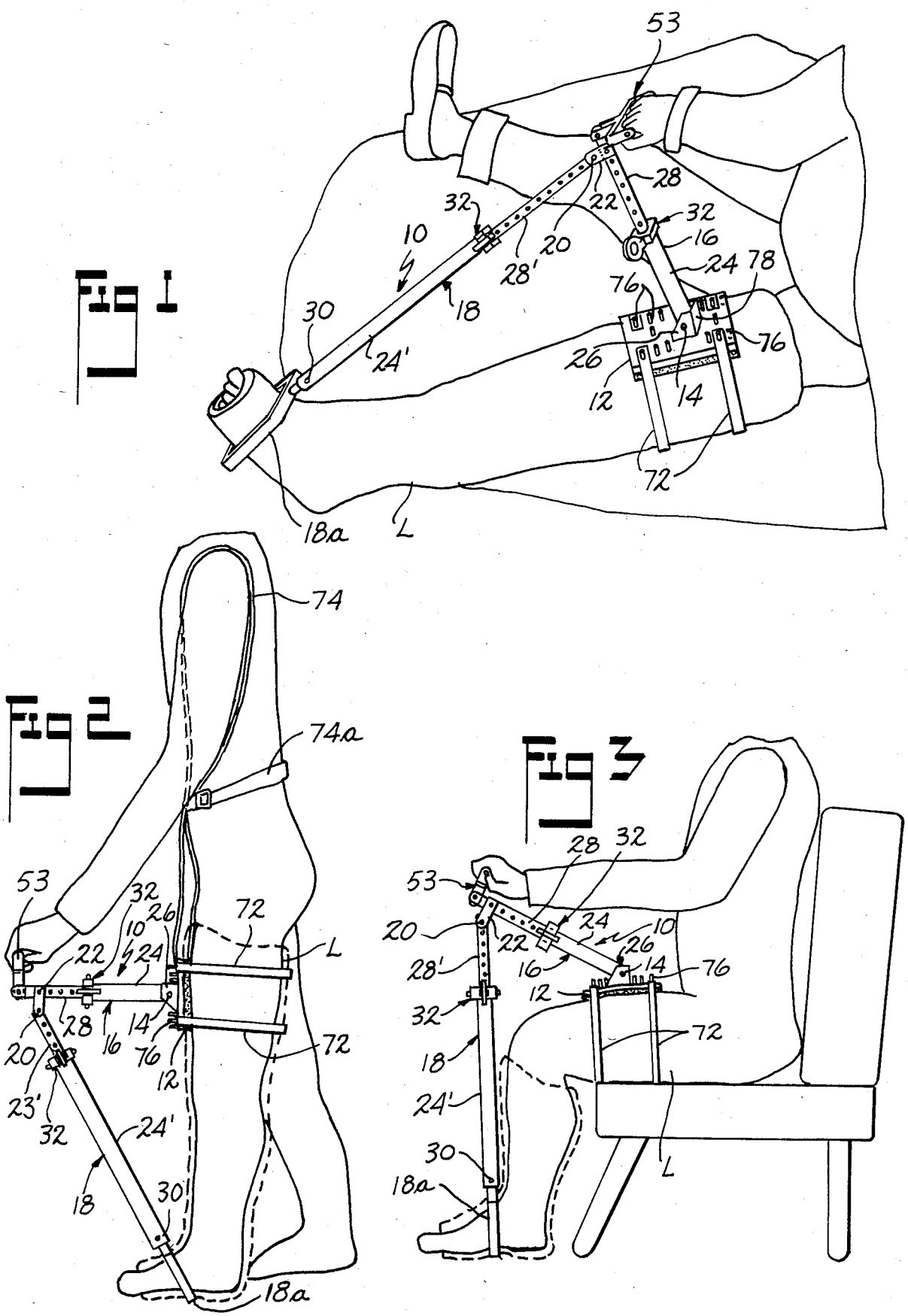

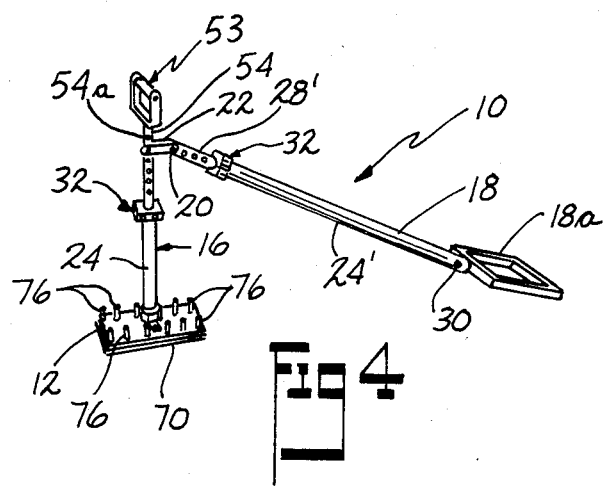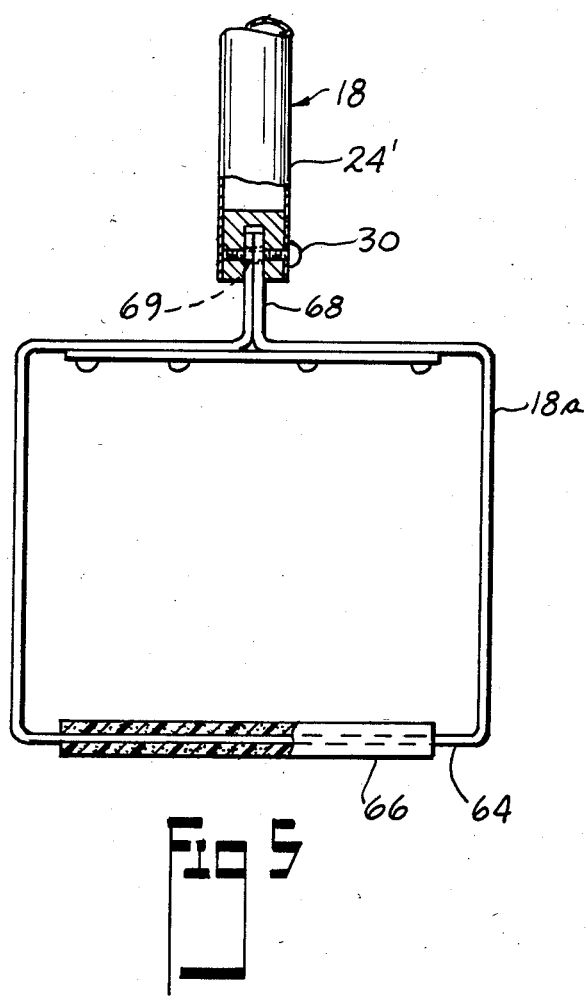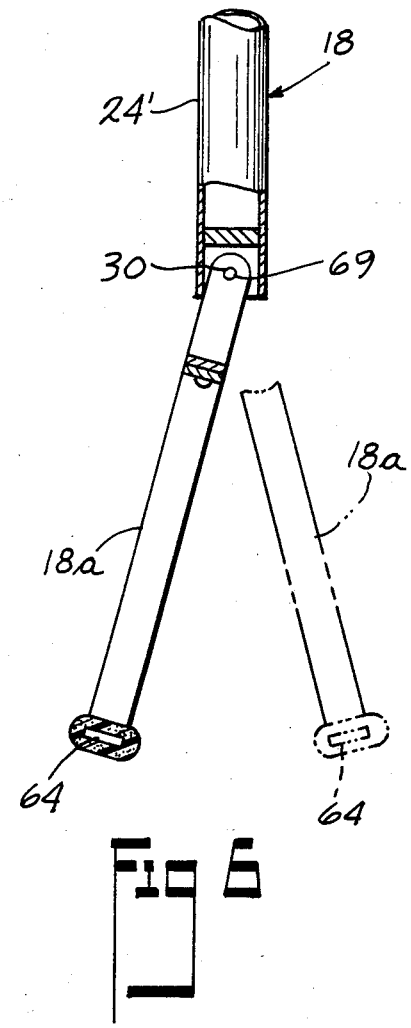

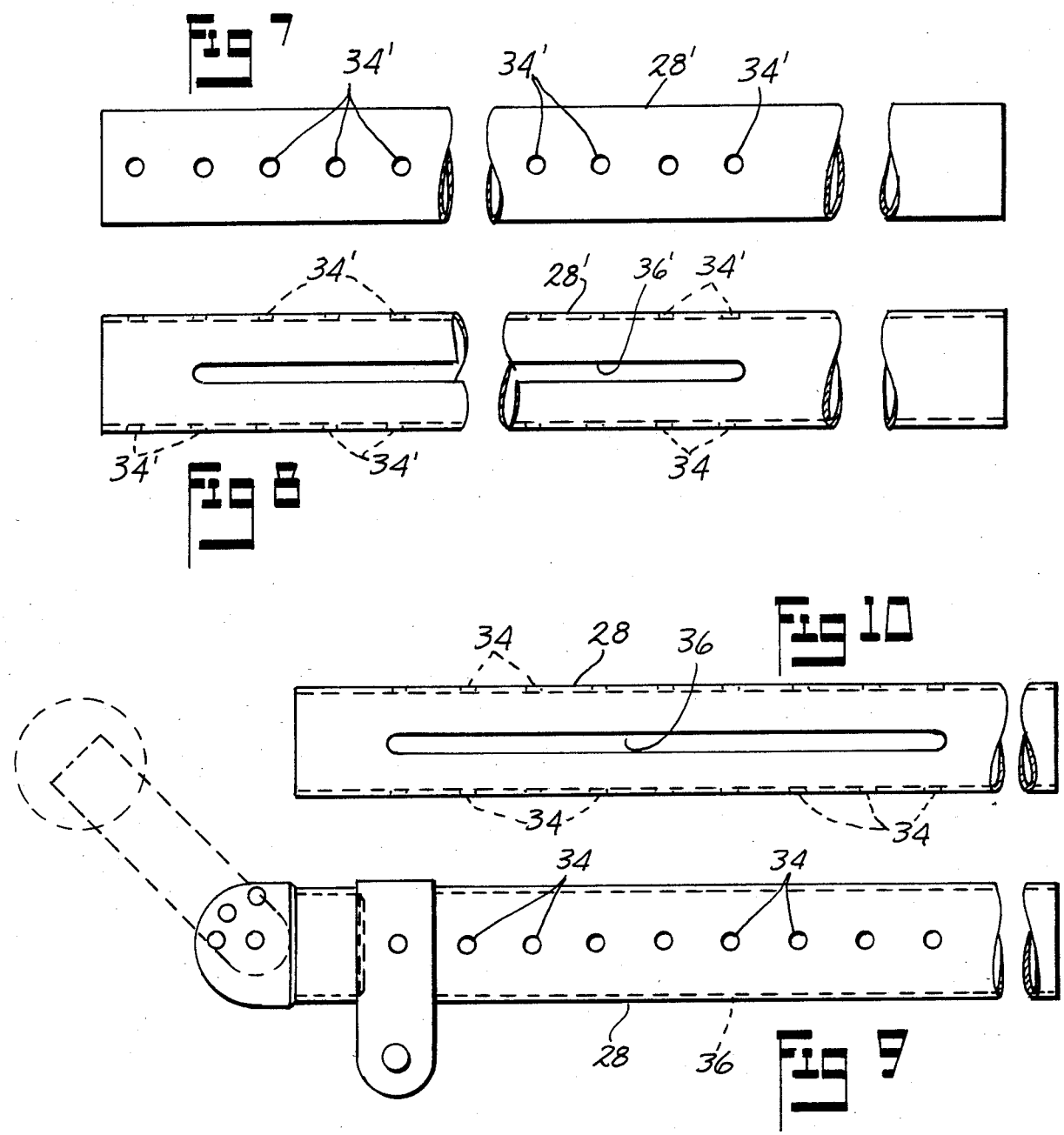

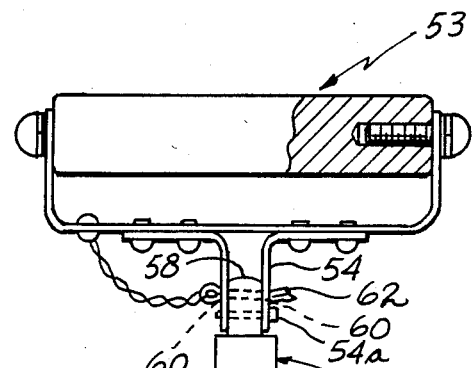
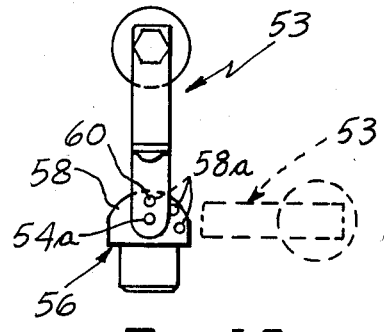
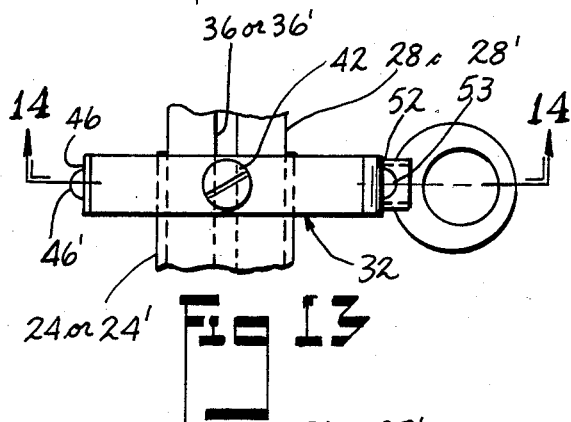
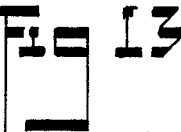
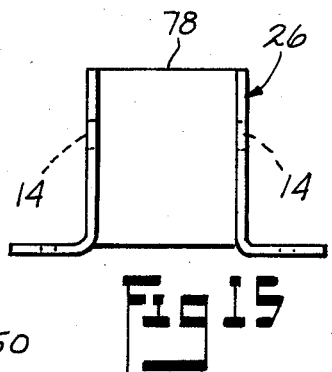
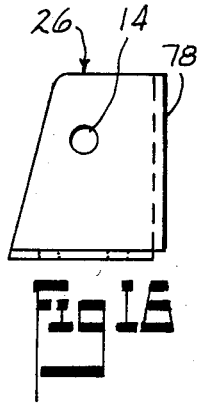
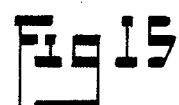
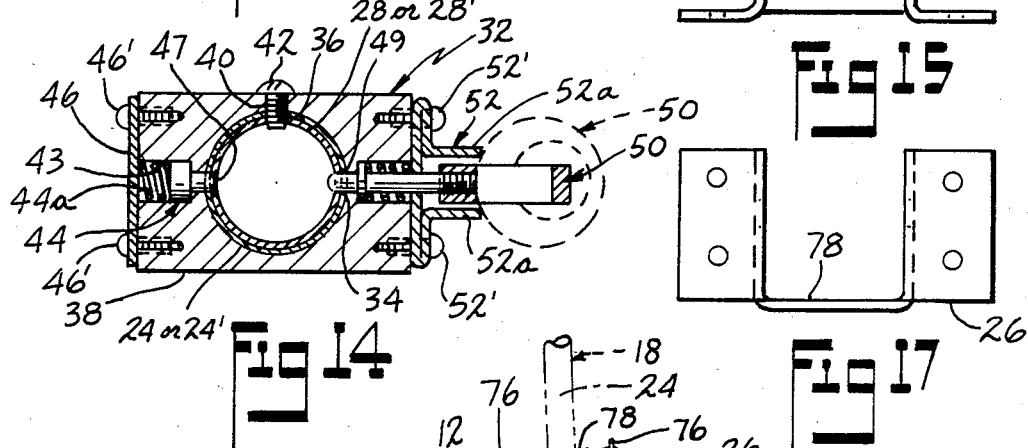
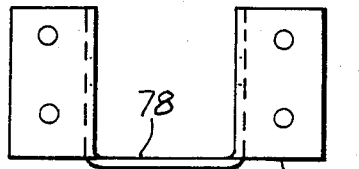
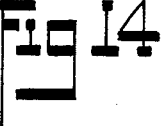
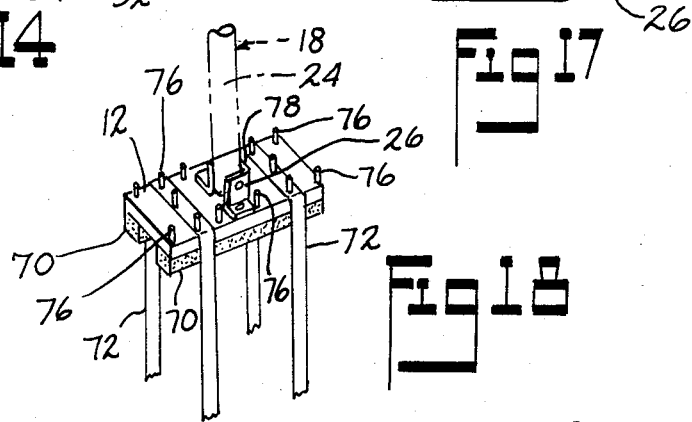
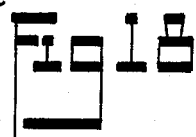

LEG MANIPULATING DEVICE

This invention relates to a limb manipulating device, and more particularly a limb manipulating device which is adjustable for expeditiously accommodating the device for use by different sizes of patients.

BACKGROUND OF THE INVENTION

There are various devices known in the prior art for facilitating the manipulation of a patient's limb which if it is encased in a cast, or is weakened from disease or injury, presents substantial problems in moving or manipulating the limb.

Generally, in order to obtain any substantial manipulation of the limb, the patient usually requires help from another individual to move or manipulate the limb, and this of course results in considerable problems to a patient when the patient is alone and help is not immediately available.

In U.S. Pat. No. 2,966,905 issued Jan. 3, 1961 to A. Kamenshine and entitled Ambulation Training Apparatus, there is disclosed a device for facilitating the movement of an incapacitated or diseased limb and which includes a base adapted to be supported generally on the patient's limb, and with a lever pivoted to the base and with a sling attached to the lever and adapted for coupling to the patient's limb, for connecting the limb to the lever, thereby enabling the patient to shift the incapacitated limb by actuation of the lever.

U.S. Pat. No. 2,607,340 dated Aug. 19, 1952 to H. E. Anderson discloses a sling device for shifting an incapacitated or injured leg.

U.S. Pat. No. 4,019,503 dated Apr. 26, 1977 to Willie R. Smith discloses a device including a hand grippable handle for manipulating a casted limb.

U.S. Pat. No. 4,205,666 dated June 3, 1980 to John P. Kapp, Jr. et al discloses a levered handle having a hand sling portion for moving a disabled human limb, with the lever portion pivoting horizontally in use with respect to the handle portion.

None of these devices have been completely satisfactory and none anticipate applicants' adjustable limb manipulating device.

SUMMARY OF THE INVENTION

The present invention provides a device for facilitating the movement of a patient's incapacitated limb and which includes a base adapted to be supported on the thigh of the patient's limb, and a lever pivoted to the base, and with means attached to the lever and adapted for coupling to the patient's limb, for connecting the limb to the lever, and wherein the device includes means for selectively adjusting the lengths of the operating parts thereof, thereby providing for expeditious accommodation of the device to different sizes of patients.

Accordingly, an object of the invention is to provide a novel device for facilitating the movement by a patient of an incapacitated limb, such as for instance a casted limb or a diseased limb.

A further object of the invention is to provide a device of the aforementioned type wherein the device comprises a base adapted to be supported on the thigh of a patient's limb, with a lever pivoted to the base, and with means attached to the lever and adapted for coupling to the patient's limb for connecting the limb to the lever, and wherein the lever includes means for selectively adjusting the length of the lever, for expeditiously accommodating the device to various sizes of patients, and for use by a patient in various positions of the patient.

A still further object of the invention is to provide a device of the aforementioned type wherein the lever comprises a generally hollow primary tube pivotally coupled to the base and a generally hollow extension tube telescopically mounted relative to the primary tube, together with means for detachably locking the extension tube in selected telescoped position relative to the primary tube.

A still further object of the invention is to provide a device of the aforementioned type wherein the lifter member of the device, adapted for connecting the patient's limb to the lever, comprises a selectively extensible and retractable rod to aid in accommodating the device to different sizes of patients.

A still further object of the invention is to provide a device of the aforementioned type which is relatively light weight and non-complex in construction, and which facilitates the manipulation of and/or exercise of an incapacitated or of a diseased limb by a patient, without the need for help by another individual, thus helping to make the patient generally independent of any such additional help in attempting to move an incapacitated or diseased limb.

Other objects and advantages of the invention will be apparent from the following description taken in conjunction with the accompanying drawings, wherein:

BRIEF DESCRIPTION OF THE DRAWINGS

FIG. 1 is a generally diagrammatic fragmentary, elevational illustration of the levered device of the invention as mounted on the thigh of a patient's incapacitated leg and attached thereto, for facilitating the shifting thereof;

FIG. 2 is a generally diagrammatic fragmentary, elevational illustration of the levered device of the invention as mounted on the thigh of a patient's incapacitated leg for aiding in shifting of the incapacitated limb in an upright or walking position of the patient;

FIG. 3 is a generally diagrammatic fragmentary, elevational view of the levered device of the invention as mounted on the thigh of a sitting patient's leg and attached thereto for facilitating the exercising of or the shifting movement of a sitting patient's incapacitated limb;

FIG. 4 is a generally perspective side elevational view of the levered and extensible manipulation device of the invention;

FIG. 5 is a partially broken front elevational view of the stirrup portion coupled to the lifting rod section of the device;

FIG. 6 is a partially broken and sectional side elevational view of the stirrup portion illustrated in FIG. 5, and illustrating in phantom lines another position of the stirrup portion relative to the lifting rod portion;

FIG. 7 is a broken, reduced size side elevational view of the extender tube of the lifter rod portion of the manipulating device;

FIG. 8 is a broken side elevational view taken from the side of the extender tube illustrated in FIG. 7 after rotating the tube about its lengthwise axis approximately 90°;

FIG. 9 is a reduced size, broken side elevational view of the extender tube of the lever portion of the device, showing in phantom lines the adjustable handle;

FIG. 10 is a broken side elevational view of the tube of FIG. 9 rotated 90°;

FIG. 11 is an enlarged, partially sectioned front elevational view of the handle portion of the levered lifter device, adapted for coupling to the distal end of the lever;

FIG. 12 is a side elevational view of the handle portion of FIG. 11, showing the arrangement for selective adjustment of the position of the handle relative to the lever;

FIG. 13 is a fragmentary, enlarged elevational view showing a locater mechanism of the lifter device, adapted for mounting on the primary portion of the extensible lifter rod or on the primary portion of the lever, for detachably locking the associated extender portion to the primary portion;

FIG. 14 is a horizontal sectional view taken generally along the plane of line 14—14 of FIG. 13 looking in the direction of the arrows, and illustrating the movable locking pin of the locater in locking position; in phantom lines there is illustrated the deactivated position of the ring handle of the locking pin;

FIGS. 15, 16 and 17 are respectively front, side and bottom views of a bracket utilized for attaching the lever portion to the base portion; and FIG. 18 is a reduced size perspective view of the base portion of the lifter mechanism illustrating the cushioning strips on the underside thereof, together with detachable straps for rapidly securing the lifter device to the thigh of a patient.

DESCRIPTION OF PREFERRED EMBODIMENT

Referring now again to the drawings, and particularly to FIGS. 1 and 4 thereof, reference number 10 refers to the levered limb manipulating device of the invention. The device comprises a base 12 which is adapted to be supported on the thigh of a patient's limb L which may be encased in a cast or the like as shown, or which may merely be weakened by disease or injury, without being casted, thus presenting obvious problems in conjunction with movement of the limb, especially when the patient is alone and additional attendants are not available to come to the patient's aid.

Pivoted to the base 12 at 14, as by a transverse pivot pin, is an elongated extensible and retractable lever 16, to which is coupled a preferably extensible and retractable lifter member 18 having a stirrup portion 18a, adapted to receive therein the foot of the incapacitated limb. Lifter portion 18 may be coupled as at 20, to a bracket 22 which may be supported on and coupled to the extensible section of the lever 16.

The lever 16 comprises, in the embodiment illustrated, a generally hollow primary or pivot tube portion 24 pivotally coupled to the base preferably by bracket 26, and a generally hollow extender tube portion 28 (FIGS. 1, 9 and 10) telescopically mounted relative to the primary tube portion 24.

The lifter member likewise comprises, in the embodiment illustrated, a generally hollow primary tube portion 24' pivotally coupled as at 30 to stirrup 18a, and a generally hollow extender tube portion 28' telescopically mounted on primary tube portion 24'.

Locater means 32 (FIGS. 1, 13 and 14) is provided for detachably locking the respective extender tube portion in selected telescoped condition relative to its associated primary tube portion, as will be hereinafter described in greater detail.

The extender portion 28 of the lever 16, as best shown in FIGS. 9 and 10, on opposite sides thereof includes a series of spaced openings 34 extending transversely completely through the tube (preferably spaced equidistance from one another) and on another side thereof approximately 90 circumferential degrees from openings 34 there is provided an elongated slot 36. The extender portion 28' of lifter member 18 likewise includes a series of spaced openings 34' therein on opposite sides (FIG. 7) and on another side thereof spaced approximately 90 circumferential degrees from openings 34', an elongated slot 36' is likewise provided.

The locater mechanism 32 (FIGS. 1, 13 and 14) in the embodiment illustrated includes a housing 38 having a threaded opening 40 therein through which is inserted a threaded fastener 42 which coacts with the housing and through a complementary opening in the respective primary tube portion, to position or lock locater 32 in selected position on the respective primary tube portion 24 or 24' of both the lever 16 and the lifter member 18, and as illustrated in FIGS. 1 and 14. The inner end of fastener 42 extends through the complementary width of aforementioned slot 36 or 36' in the respective extender portion 28 or 28' to limit rotary movement of the extender portion with respect to the respective primary tube portion 24 or 24'.

One side of the housing 38 has a spring loaded click pin 44 positioned in a recess 43 in the housing with the pin adapted to be urged by the associated compression spring 44a in a direction inwardly of the housing, with the pin 44 being received through a confronting opening 45 in the primary tube portion 24 or 24' of the lever 16 and the lifter member 18, and just into a confronting one of the series of openings 34 or 34' in the associated extender tube portion 28 or 28', for aiding in positioning of the respective extender tube portion relative to its associated primary tube portion. Pin 44 and its associated spring is preferably maintained in assembled relationship with the housing 38 of the locater by means of removable retainer plate 46 and associated fasteners 46'. Click pin 44 has a rounded end 47 which is just slightly received in the associated opening in the extender tube portion 28 or 28' and as will be hereinafter discussed.

The other side of housing 38 is provided with a spring loaded cylindrical locking pin 48 which is received through a complementary opening 49 in the primary tube portion 24 or 24' and into and completely through a selected confronting one of the spaced series of openings 34 or 34' on the corresponding side of the respective extender tube portion 28 or 28' to thus provide for releasably locking the extender tube portion 28 or 28' in selected extended or retracted condition with respect to its associated primary tube portion.

Pin 48 is provided with a handle 50, and a bracket 52 is secured as by means of fasteners 52' to the housing, and with the handle 50 being received between the spaced upstanding ears 52a on bracket 52, in the locking position of the locking pin, as illustrated in FIGS. 13 and 14. When it is desired to move the locking pin 48 to unlocking position, the handle 50 is grasped and moved axially against the resistance to compression of the associated spring, to withdraw the nose of the locking pin from its received condition in one of the openings 34 or 34' in the confronting side of the associated extender tube 28 or 28'. The handle portion 50 can be supported on the ears 52a and thus be maintained in such an unlocked condition, and as illustrated in phantom lines in FIG. 14.

Thus it will be seen that the locater mechanism 32 enables a patient to grasp the handle 50 and unlock the locking pin 48, move the extender tube or tubes to selected position, and then rotate the handle 50 90° to permit the handle to move back between ears 52a and the locking pin to re-enter into locking coaction between the extender and primary tubes, thus providing for expeditious adjusting of the length of either or both the lifter member 18 and the lever member 16. Aforementioned click pin 44 is automatically deactivated upon movement of locking pin 48 to unlocked position and moving extender tube portion 28 or 28' lengthwise relative to the primary portion 24 or 24' until relocking of locking pin 48 occurs at the selected extended or retracted position of the extender tube portion, whereupon spring 44a causes automatic positioning of the click pin in the confronting opening 34 or 34' on the corresponding side of the extender tube 28 or 28'. The rounded end 47 of the click pin enables it to be cammed back against the resistance to compression of spring 44a during lengthwise movement of the extender tube portion.

Secured to the outer distal end of the lever 16 is a handle portion 53 (FIGS. 1, 11 and 12) with the handle in the embodiment illustrated, being of generally D-shaped in front elevation (FIG. 11) having a projecting mounting bracket 54, which is pivoted as at 54a to cap portion 56, which is adapted to be received in tight, fixed condition in the distal end of the extender tube portion 28 of lever 16.

Cap portion 56 preferably has a central web 58 having a plurality of openings 58a formed therein disposed along an arc on said central web, and with the handle bracket projection 54 having aligned openings 60 therein, which are adapted to be registered with a selected one of the openings 58a in the web 58, and with a removable locking pin 62 provided for receipt through openings 60 and the selected opening 58a, to lock the handle 53 in selected projecting position relative to the distal end of the lever, and as illustrated for one position in phantom lines in FIG. 12.

Thus it will be seen that the handle can be selectively moved to its most expeditious position with respect to the lever, depending on the desires and the use to which the lifter device 10 is being put. For instance, in a patient position as illustrated for instance in FIG. 1, the handle may be generally diagonally arranged with respect to the lever 16, while in a walking or standing position of a patient as illustrated for instance in FIG. 2, the lifter device may be more expeditiously utilized when the handle is disposed at approximately 90° to the distal end of the lever.

Referring now in particular to FIGS. 5 and 6, the stirrup portion 18a is preferably pivoted to the distal end of the primary tube portion 24' of lifter portion 18, with such stirrup portion being preferably provided on its lowermost transverse run 64 with a friction-type coating 66, which may be of vinyl plastic or the like, for aiding in preventing slippage with respect to a floor surface, when the patient is moving with the device along a floor surface. As can be seen in FIG. 6, the upper end of the projection 68 on the stirrup 18a is received in attached relation as at 69, within the distal end of the primary tube 24' which provides for limited pivotal movement of the stirrup 18a with respect to tube 24'. This facilitates movement by the patient of the limb when he is utilizing the device.

Referring now to FIGS. 4 and 18, the base 12 is preferably provided with some type of cushioning means, such as for instance spaced strips of sponge rubber or plastic foam 70 secured to its underside, for cushioning the mounting of the base on the patient's thigh. Straps 72 which may have buckles or may be of the Velcro fastening type, are preferably provided for securing the lifter device to the thigh of the patient especially, in the event that the patient is going to move about with the lifter device as shown for instance in FIG. 2. Also in the walking position of the patient, there may be provided a shoulder and waist strap 74, 74a secured to the base portion 12 of the lifter, for aiding in facilitating maintenance of the lifter device in coacting relation with the thigh of the patient, especially if the straps 72 are not utilized.

In this connection, the base may have a plurality of pins 76 projecting from the upper surface thereof adapted to be received through openings in the straps for rapidly fastening and unfastening the attaching straps to the lifter device and to the patient, as well as providing for ready removal of such straps, in the event that it is desired to utilize the lifter device without attaching strap means. Pins 76 are adapted to be received in generally snug relation through the receiving openings in the associated straps.

The primary tube portion 24 of the lever 16 is preferably pivoted to the base 12 by means of aforementioned bracket 26 secured to the base by suitable fasteners, and which includes a rear wall section 78 which is adapted for engagement with the primary tube portion in the generally perpendicular position of the lever with respect to the plane of the base, so that the lever is restricted in further rearward pivotal movement with respect to the base, upon actuation by the patient. Such an arrangement does not prevent or limit pivotal movement of the lever in a forward direction relative to the base, but ensures that the lever can be pivoted only to approximately a 90° position with respect to the base in a rearward direction.

The lifter device is preferably formed of aluminum tubing and aluminum parts except for the base 12 which may be formed of any suitable material, such as a plastic, and which facilitates its lightness and thereby makes it more convenient and comfortable for use by a patient.

From the foregoing description and accompanying drawings, it will be seen that the invention provides a novel manipulating device for facilitating movement by a patient of an incapacited or weakened limb, and comprising a base adapted to be supported on the thigh of the patient's limb with an extendible lever pivoted to the base and means attached to the lever and adapted for coupling to the patient's limb generally adjacent the distal end thereof, for connecting the limb to the lever, thereby enabling the patient to shift the incapacited limb by actuation of the lever, and without the need of assistance from another person or attendant, and wherein the lifter device can be accommodated to different sizes and ages of patients.

The terms and expressions which have been used are used as terms of description and not of limitation, and there is no intention in the use of such terms and expressions of excluding any equivalents of any of the features shown or described, or portions thereof, and it is recognized that various modifications are possible within the scope of the invention claimed.

We claim:

1. A device for facilitating movement by a patient of an incapacitated limb of the patient comprising a base adapted to be supported on the thigh of the patient's limb, a lever pivoted to said base, means attached to said lever and adapted for coupling to the patient's limb generally adjacent the distal end thereof, for connecting the limb to said lever, thereby enabling the patient to shift the incapacitated limb by actuation of said lever, and said lever includes means for selectively adjusting the length of said lever for accommodating the device to different sizes of patients, and wherein said lever at the distal end thereof includes a projecting handle portion, and means for selectively changing the projecting position of said handle portion relative to the remainder of said lever.

2. A device in accordance with claim 1 wherein the first mentioned means comprises a stirrup into which the incapacitated limb is adapted to be inserted, and friction means on the lower portion of said stirrup for aiding in preventing slippage of said stirrup on a floor surface.

3. A device in accordance with claim 1 wherein the first mentioned means comprises a stirrup portion adapted to receive the foot of the incapacitated limb together with a selectively adjustable in length, rod portion coupling the stirrup portion to said lever.

4. A device in accordance with claim 1 wherein the first mentioned means comprises a stirrup portion adapted to receive the foot of the incapacitated limb together with a generally rigid but selectively adjustable in length, lifter rod portion movably attached at one end thereof to said stirrup portion, and movably coupled at the other end thereof to said lever.

5. A device in accordance with claim 1 wherein said base includes cushioning means thereon for padding said base for comfortable positioning of the latter on the thigh of the patient.

6. A device in accordance with claim 1 wherein the second mentioned means comprises a generally hollow pivot tube pivotally coupled to said base and a generally hollow extension tube telescopically mounted relative to said pivot tube, and means for detachably locking said extension tube in selected telescoped condition relative to said pivot tube to provide the adjustable length lever, and wherein the first mentioned means is movably attached to said extension tube of said lever.

7. A device in accordance with claim 1 wherein the first mentioned means comprises a selectively extensible and retractable lifter rod portion connected at one end to said lever and including means on the other end thereof for coupling the device to the foot of the patient, said rod portion including a first tubular-like portion coupled to the last mentioned means and a second tubular-like portion telescopically mounted relative to said first tubular-like portion and adapted for selective extension and retraction to vary the length of said rod portion, and means for releasably locking said first and said second tubular-like portions in selected telescoped condition relative to one another.

8. A device in accordance with claim 7 wherein the last mentioned means comprises a locater device secured to said lifter rod portion and mounting a selectively movable retainer pin for coaction between said first and said second tubular-like portions to maintain the latter in predetermined telescoped relation.

9. A device in accordance with claim 1 wherein said handle portion has a mounting projection thereon pivoted to said distal end of said lever, said means for changing the position of said handle portion comprising an opening in said projection adapted for selective alignment with an aligned one of a series of openings on said lever end, and a locking pin removably received in the aligned openings on said handle projection and on said lever end to releasably lock said handle in selected projecting position relative to said lever end.

10. A device in accordance with claim 1 wherein said lever comprises a pivot portion pivoted to said base at one end thereof, and an extension portion telescopically mounted on said pivot portion, for selectively adjusting the length of said lever, said extension portion having a series of spaced openings therein spaced lengthwise of said extension portion, and a spring loaded detent mounted on said pivot portion and adapted to be received in a confronting one of said openings in said extension portion, to detachably lock said extension portion in selected telescoped position of said extension portion relative to said pivot portion.

11. A device in accordance with claim 10 wherein said extension and said pivot portions are formed of hollow circular in transverse cross section, tubing, and wherein said extension portion includes a slot running lengthwise of said extension portion, and means coacting between said pivot portion and said extension portion and received in said slot for preventing rotational movement of said extension portion relative to the lengthwise axis of said pivot portion, while permitting telescoping movement of said extension portion relative to said pivot portion upon deactivation of said locking detent.

12. A device in accordance with claim 1 wherein the second mentioned means comprises a primary portion of said lever pivoted to said base at one end thereof and an extension portion of said lever mounted for telescoping movement relative to said primary portion, for selectively adjusting the length of said lever, and means for releasably locking said extension lever portion in selected telescoped condition relative to said primary lever portion.

13. A device in accordance with claim 12 wherein the last mentioned means comprises a housing mounted on said primary portion and containing a spring loaded detent adapted for coaction with a selected one of a series of openings in said extension portion, for releasably holding said extension portion in selected telescoped condition relative to said primary portion.

14. A device in accordance with claim 13 wherein said extension and said primary portions are hollow tubes, said housing also comprising another spring loaded detent coacting with a confronting one of another series of openings in said extension portion for aiding in locating said extension portion relative to said primary portion, the last mentioned detent being deactivateable upon deactuation of the first mentioned detent and moving said extension portion telescopically relative to said primary portion.

15. A device for facilitating movement by a patient of an incapacitated limb of the patient comprising a base adapted to be supported on the thigh of the patient's limb, a lever pivoted to said base, means attached to said lever and adapted for coupling to the patient's limb generally adjacent the distal end thereof, for connecting the limb to said lever, thereby enabling the patient to shift the incapacitated limb by actuation of said lever, and said lever includes means for selectively adjusting the length of said lever for accommodating the device to different sizes of patients, and wherein said lever includes a separate handle portion pivoted to said lever adjacent the outer end of said lever, and means for releasably maintaining said handle portion in selected pivoted position on said lever.

16. A device for facilitating movement by a patient of an incapacitated limb of the patient comprising a base adapted to be supported on the thigh of the patient's limb, a lever pivoted to said base, means attached to said lever and adapted for coupling to the patient's limb generally adjacent the distal end thereof, for connecting the limb to said lever, thereby enabling the patient to shift the incapacitated limb by actuation of said lever, and said lever includes means for selectively adjusting the length of said lever for accommodating the device to different sizes of patients, the second mentioned means comprising a primary portion of said lever pivoted to said base at one end thereof and an extension portion of said lever mounted for telescoping movement relative to said primary portion for selectively adjusting the lenght of said lever, and means for releasably locking said extension lever portion in selected telescoped condition relative to said primary lever portion, the last mentioned means comprising a housing mounted on said primary portion and containing a spring loaded detent adapted for coaction with a selected one of a series of openings in said extension portion for releasably holding said extension portion in selected telescoped condition relative to said primary portion, said extension and said primary portions being hollow tubes, said housing also comprising another spring loaded detent coacting with a confronting one of another series of openings in said extension portion for aiding in locating said extension portion relative to said primary portion, the last mentioned detent being deactivateable upon deactuation of the first mentioned detent and moving said extension portion telescopically relative to said primary portion, and wherein said extension portion of said lever at the distal end thereof includes a projecting handle portion, and means for selectively changing the projecting position of said handle portion relative to said lever.

17. A device in accordance with claim 16 including means on said housing coacting with said primary and said extension portions for preventing rotational movement of said extension portion relative to said primary portion while permitting guided telescopic movement of said extension portion relative to said primary portion upon deactuation of said holding detent.

* * * * *